US012608828B2

(12) United States Patent
Wang

(10) Patent No.: US 12,608,828 B2
(45) Date of Patent: Apr. 21, 2026

(54) IMAGE PROCESSING APPARATUS, OPERATION METHOD OF IMAGE PROCESSING APPARATUS, OPERATION PROGRAM OF IMAGE PROCESSING APPARATUS, AND TRAINED MODEL

(71) Applicant: FUJIFILM Corporation, Tokyo (JP)

(72) Inventor: Caihua Wang, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 469 days.

(21) Appl. No.: 18/184,690

(22) Filed: Mar. 16, 2023

(65) Prior Publication Data

US 2023/0222675 A1 Jul. 13, 2023

Related U.S. Application Data

(63) Continuation of application No. PCT/JP2021/033189, filed on Sep. 9, 2021.

(30) Foreign Application Priority Data

Sep. 28, 2020 (JP) ................................. 2020-162678

(51) Int. Cl.
*G06K 9/00* (2022.01)
*G06T 7/00* (2017.01)
(Continued)

(52) U.S. Cl.
CPC .............. *G06T 7/30* (2017.01); *G06T 7/0012* (2013.01); *G06V 10/761* (2022.01);
(Continued)

(58) Field of Classification Search
None
See application file for complete search history.

(56) References Cited

U.S. PATENT DOCUMENTS

| 6,915,003 B2 | 7/2005 | Oosawa |
| 10,980,493 B2 | 4/2021 | Osawa |

(Continued)

FOREIGN PATENT DOCUMENTS

| EP | 3686805 | 7/2020 |
| JP | 2002032735 | 1/2002 |

(Continued)

OTHER PUBLICATIONS

Ava Assadi Abolvardi et al., "Registration Based Data Augmentation for Multiple Sclerosis Lesion Segmentation", 2019 Digital Image Computing: Techniques and Applications (DICTA), Dec. 2, 2019, pp. 1-5.

(Continued)

*Primary Examiner* — Wei Wen Yang
(74) *Attorney, Agent, or Firm* — JCIPRNET

(57) ABSTRACT

An image processing apparatus includes a processor and a memory connected to or built in the processor. The processor is configured to perform non-linear registration processing on a first medical image and a second medical image among a plurality of medical images, and generate at least one new medical image that is used for training a machine learning model for the medical images by transforming at least one medical image of the first medical image or the second medical image based on a result of the non-linear registration processing.

12 Claims, 11 Drawing Sheets

(51) Int. Cl.

| | | |
|---|---|---|
| *G06T 7/30* | (2017.01) |
| *G06V 10/74* | (2022.01) |
| *G06V 10/764* | (2022.01) |
| *G16H 30/40* | (2018.01) |
| *G16H 50/20* | (2018.01) |

(52) U.S. Cl.

CPC ........... *G06V 10/764* (2022.01); *G16H 30/40* (2018.01); *G16H 50/20* (2018.01); *G06T 2207/10088* (2013.01); *G06T 2207/20081* (2013.01); *G06T 2207/30016* (2013.01)

(56) References Cited

U.S. PATENT DOCUMENTS

| | | | |
|---|---|---|---|
| 11,096,643 B2 | 8/2021 | Takei | |
| 2020/0118265 A1 | 4/2020 | Igarashi | |
| 2020/0327370 A1 | 10/2020 | Masuda et al. | |
| 2021/0390282 A1* | 12/2021 | Lin ........................... | G06T 7/97 |
| 2023/0005140 A1* | 1/2023 | Ferl ...................... | G06V 10/774 |

FOREIGN PATENT DOCUMENTS

| | | |
|---|---|---|
| JP | 2018175227 | 11/2018 |
| JP | 2019195426 | 11/2019 |
| JP | 2020058590 | 4/2020 |
| WO | 2019069867 | 4/2019 |

OTHER PUBLICATIONS

Kevin P. Nguyen et al., "Anatomically-Informed Data Augmentation for functional MRI with Applications to Deep Learning", Proceedings of SPIE—the International Society for Optical Engineering, Mar. 10, 2020, pp. 1-5, vol. 11313.

Amy Zhao et al., "Data augmentation using learned transformations for one-shot medical image segmentation", Computer Vision and Pattern Recognition, Feb. 25, 2019, pp. 1-12.

Philip Novosad et al., "Accurate and robust segmentation of neuroanatomy in TI-weighted MRI by combining spatial priors with deep convolutional neural networks", Human brain mapping, Oct. 21, 2019, pp. 1-22, vol. 41, No. 2.

David G. Ellis et al., "Deep Learning Using Augmentation via Registration: 1st Place Solution to the AutoImplant 2020 Challenge", Topics in Cryptology-CT-RSA2020: The Cryptographers' Track at the RSA Conference, Dec. 4, 2020, pp. 47-55, vol. 12439.

"Search Report of Europe Counterpart Application", issued on Mar. 4, 2024, p. 1-p. 11.

"Office Action of Japan Counterpart Application", issued on Dec. 19, 2023, with English translation thereof, p. 1-p. 6.

"International Search Report (Form PCT/ISA/210) of PCT/JP2021/033189", mailed on Oct. 12, 2021, with English translation thereof, pp. 1-5.

"Written Opinion of the International Searching Authority (Form PCT/ISA/237) of PCT/JP2021/033189", mailed on Oct. 12, 2021, with English translation thereof, pp. 1-6.

Connor Shorten et al., "A survey on Image Data Augmentation for Deep Learning," Journal of Big Data, Jul. 2019, pp. 1-49.

Yuji Tokozume et al., "Between-class Learning for Image Classification," 2018 IEEE/CVF Conference on Computer Vision and Pattern Recognition (CVPR), Jun. 2018, pp. 5486-5494.

Gregory Kuling et al., "Data Augmentation with Conditional Generative Adversarial Networks for Improved Medical Image Segmentation," Proc. Intl. Soc. Mag. Reson. Med., Aug. 2020, pp. 1-3.

Ryoma Aoki et al., "Differences in Results provided by Teaching Data on Cartilage Extraction in Knee MR Images by Using Deep Learning," IEICE Technical Report, Feb. 2019, pp. 1-8.

* cited by examiner

OUTPUT TRANSFORMATION
AMOUNT AS PROCESSING RESULT

FIG. 8A

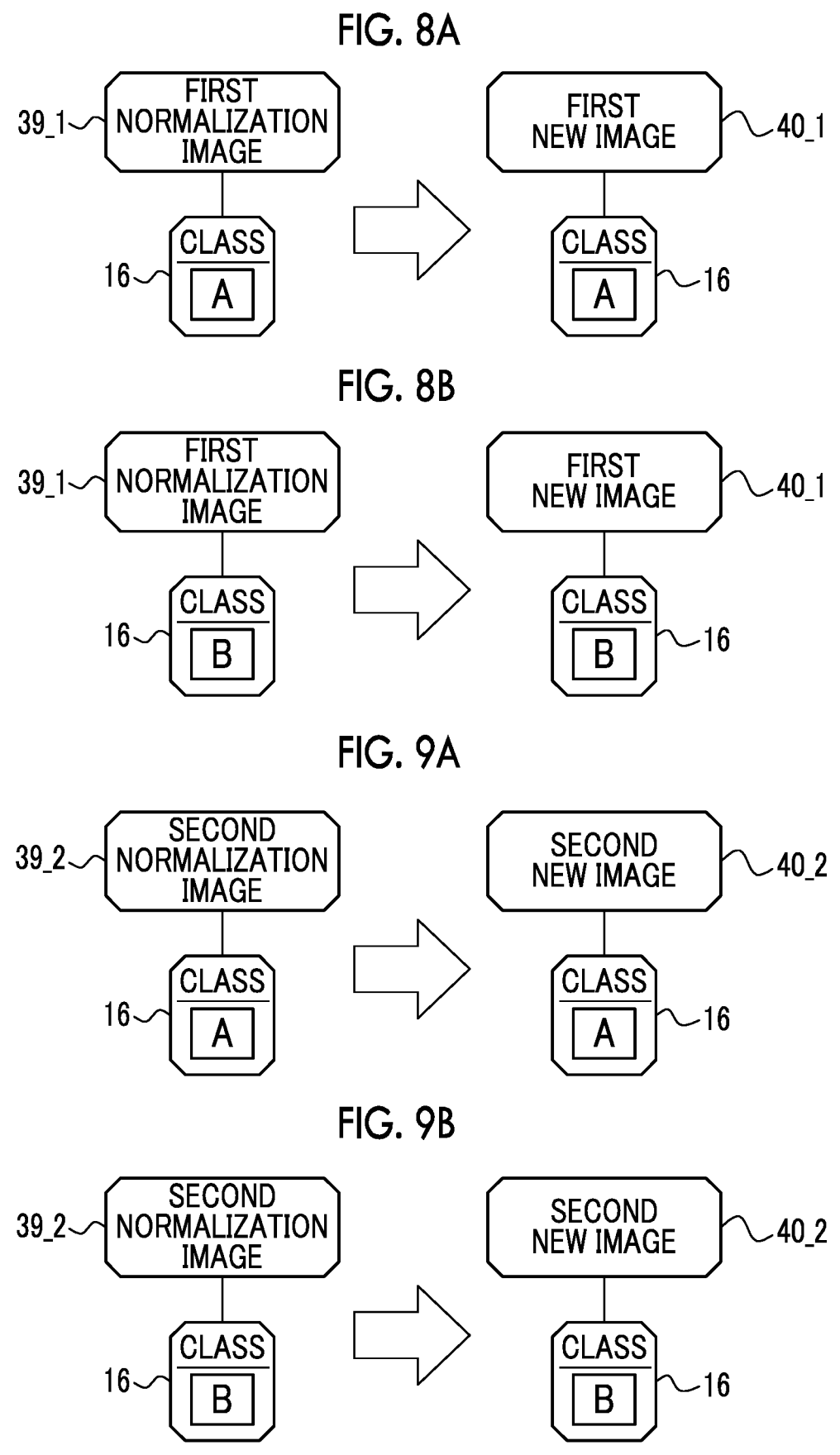

39_1 — FIRST NORMALIZATION IMAGE

16 — CLASS A

⟹

FIRST NEW IMAGE — 40_1

CLASS A — 16

FIG. 8B

39_1 — FIRST NORMALIZATION IMAGE

16 — CLASS B

⟹

FIRST NEW IMAGE — 40_1

CLASS B — 16

FIG. 9A

39_2 — SECOND NORMALIZATION IMAGE

16 — CLASS A

⟹

SECOND NEW IMAGE — 40_2

CLASS A — 16

FIG. 9B

39_2 — SECOND NORMALIZATION IMAGE

16 — CLASS B

⟹

SECOND NEW IMAGE — 40_2

CLASS B — 16

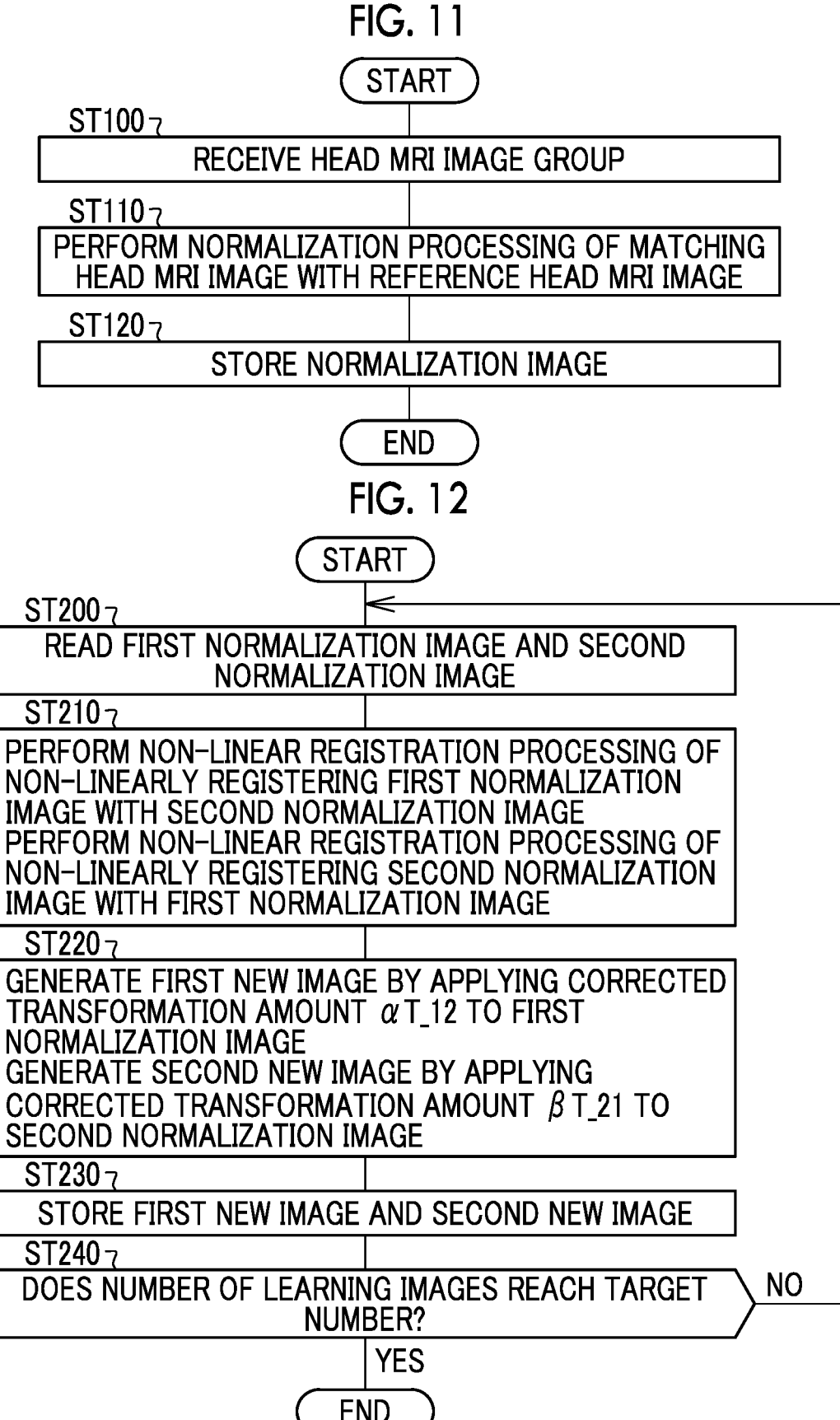

FIG. 11

START

ST100
RECEIVE HEAD MRI IMAGE GROUP

ST110
PERFORM NORMALIZATION PROCESSING OF MATCHING HEAD MRI IMAGE WITH REFERENCE HEAD MRI IMAGE

ST120
STORE NORMALIZATION IMAGE

END

FIG. 12

START

ST200
READ FIRST NORMALIZATION IMAGE AND SECOND NORMALIZATION IMAGE

ST210
PERFORM NON-LINEAR REGISTRATION PROCESSING OF NON-LINEARLY REGISTERING FIRST NORMALIZATION IMAGE WITH SECOND NORMALIZATION IMAGE
PERFORM NON-LINEAR REGISTRATION PROCESSING OF NON-LINEARLY REGISTERING SECOND NORMALIZATION IMAGE WITH FIRST NORMALIZATION IMAGE

ST220
GENERATE FIRST NEW IMAGE BY APPLYING CORRECTED TRANSFORMATION AMOUNT $\alpha T\_12$ TO FIRST NORMALIZATION IMAGE
GENERATE SECOND NEW IMAGE BY APPLYING CORRECTED TRANSFORMATION AMOUNT $\beta T\_21$ TO SECOND NORMALIZATION IMAGE

ST230
STORE FIRST NEW IMAGE AND SECOND NEW IMAGE

ST240
DOES NUMBER OF LEARNING IMAGES REACH TARGET NUMBER?    NO

YES

END

FIG. 14

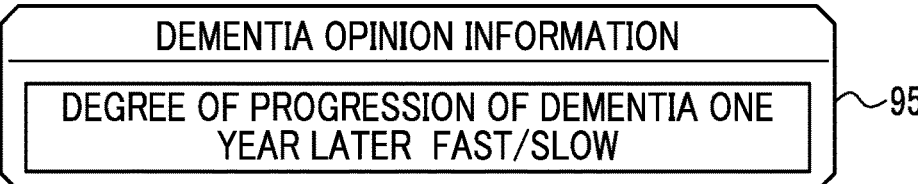

DEMENTIA OPINION INFORMATION

DEGREE OF PROGRESSION OF DEMENTIA ONE YEAR LATER  FAST/SLOW ～95

FIG. 15

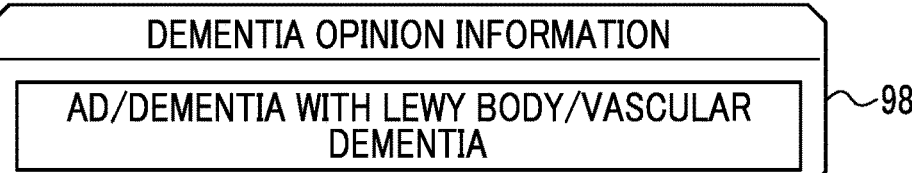

DEMENTIA OPINION INFORMATION

AD/DEMENTIA WITH LEWY BODY/VASCULAR DEMENTIA ～98

FIG. 16

NORMAL DISTRIBUTION GROUP ～72

CASE WHERE CLASSES ARE SAME

FIRST $\alpha$ NORMAL DISTRIBUTION $\alpha$

MEAN $\mu$ = 0.5
STANDARD DEVIATION $\sigma$ = 0.2

73

SECOND $\alpha$ NORMAL DISTRIBUTION $\alpha$

MEAN $\mu$ = 0.2
STANDARD DEVIATION $\sigma$ = 0.2

75

CASE WHERE CLASSES ARE DIFFERENT FROM EACH OTHER

48

TRANSFORMATION COEFFICIENT GENERATION UNIT ～70

50

PROCESSING RESULT

TRANSFORMATION AMOUNT
T_12 (X, Y, Z)

TRANSFORMATION COEFFICIENT
$\alpha$ (X, Y, Z)

71

CALCULATION UNIT

39_1

FIRST NORMALIZATION IMAGE
I_1(X,Y,Z)

X

CORRECTED TRANSFORMATION AMOUNT
$\alpha$ T_12(X,Y,Z)

=

40_1

FIRST NEW IMAGE
I_1N(X,Y,Z)

TO RW CONTROL UNIT

NEW IMAGE GENERATION UNIT

IMAGE PROCESSING APPARATUS, OPERATION METHOD OF IMAGE PROCESSING APPARATUS, OPERATION PROGRAM OF IMAGE PROCESSING APPARATUS, AND TRAINED MODEL

CROSS-REFERENCE TO RELATED APPLICATIONS

This application is a continuation application of International Application No. PCT/JP2021/033189 filed on Sep. 9, 2021, the disclosure of which is incorporated herein by reference in its entirety. Further, this application claims priority from Japanese Patent Application No. 2020-162678 filed on Sep. 28, 2020, the disclosure of which is incorporated herein by reference in its entirety.

BACKGROUND

1. Technical Field

A technique of the present disclosure relates to an image processing apparatus, an operation method of an image processing apparatus, an operation program of an image processing apparatus, and a trained model.

2. Description of the Related Art

In a medical field, with a recent progress of artificial intelligence techniques, various techniques of inputting medical images to a machine learning model and outputting a disease opinion from the machine learning model have been proposed.

In the machine learning model for the medical images, a plurality of learning images are sequentially input and learned. As the number of the learning images is smaller, the number of times of learning is also reduced. As a result, it is difficult to improve prediction accuracy of a disease opinion. For this reason, in the related art, a technique of increasing the number of the learning images by using a data expansion method called data augmentation is used.

As the data expansion method, for example, a method of generating a new image by performing, on one image, various processing such as parallel displacement, rotation, enlargement/reduction, inversion, cropping, and noise addition as described in <C. Shorten, T. M. Khoshgofttar: A survey on Image Data Augmentation, Journal of Big Data, 2019> is well known. In addition, a method of generating a new image by synthesizing two different images as described in <Y. Tokozume, Y. Ushiku, T. Harada: Between-class Learning for Image Classification, CVPR, 2018> has also been proposed. The new image in this case is, for example, an image obtained by averaging pixel values of pixels of two different images.

SUMMARY

However, in the method described in <C. Shorten, T. M. Khoshgofttar: A survey on Image Data Augmentation, Journal of Big Data, 2019>, only an image similar to one target image is generated. As a result, a variation of the learning image is not increased.

In addition, the method described in <Y. Tokozume, Y. Ushiku, T. Harada: Between-class Learning for Image Classification, CVPR, 2018> is not suitable to be used for a medical image for the following reasons. That is, in a medical image, various anatomical structures that can be used as a reference when obtaining a disease opinion appear. However, in the method described in <Y. Tokozume, Y. Ushiku, T. Harada: Between-class Learning for Image Classification, CVPR, 2018>, a form having an anatomical structure is blurred. In a case where a medical image in which a form having an anatomical structure is blurred is used as the learning image, reliability of a disease opinion that is output from the machine learning model is decreased.

An embodiment according to the technique of the present disclosure provides an image processing apparatus, an operation method of an image processing apparatus, an operation program of an image processing apparatus, and a trained model capable of generating a comprehensive learning image in which a form having an anatomical structure is maintained.

According to an aspect of the present disclosure, there is provided an image processing apparatus including: a processor; and a memory connected to or built in the processor, in which the processor is configured to perform non-linear registration processing on a first medical image and a second medical image among a plurality of medical images, and generate at least one new medical image that is used for training a machine learning model for the medical images by transforming at least one medical image of the first medical image or the second medical image based on a result of the non-linear registration processing.

Preferably, the processor is configured to set the first medical image as a first new medical image by applying, to the first medical image, a corrected transformation amount $\alpha T\_12$ obtained by multiplying a transformation amount $T\_12$ from the first medical image to the second medical image in the non-linear registration processing by a transformation coefficient $\alpha$, and set the second medical image as a second new medical image by applying, to the second medical image, a corrected transformation amount $\beta T\_21$ obtained by multiplying a transformation amount $T\_21$ from the second medical image to the first medical image in the non-linear registration processing by a transformation coefficient $\beta$.

Preferably, the medical images are classified into classes, and the processor is configured to change values of the transformation coefficients $\alpha$ and $\beta$ depending on whether classes of the first medical image and the second medical image are the same or different from each other.

Preferably, the processor is configured to set a class of the first new medical image to be the same as the class of the first medical image, and set a class of the second new medical image to be the same as the class of the second medical image.

Preferably, the transformation coefficients $\alpha$ and $\beta$ are random numbers according to a normal distribution.

Preferably, a mean of a normal distribution in a case where the classes of the first medical image and the second medical image are different from each other is smaller than a mean of a normal distribution in a case where the classes of the first medical image and the second medical image are the same.

Preferably, the processor is configured to perform normalization processing of matching the first medical image and the second medical image with a reference medical image prior to the non-linear registration processing.

Preferably, the medical image is an image in which a head of a patient appears, and the machine learning model is a model that outputs a dementia opinion on the patient.

According to another aspect of the present disclosure, there is provided an operation method of an image processing apparatus, the method including: performing non-linear registration processing on a first medical image and a second medical image among a plurality of medical images; and generating at least one new medical image that is used for training a machine learning model for the medical images by transforming at least one medical image of the first medical image or the second medical image based on a result of the non-linear registration processing.

According to still another aspect of the present disclosure, there is provided an operation program of an image processing apparatus, the program causing a computer to execute a process including: performing non-linear registration processing on a first medical image and a second medical image among a plurality of medical images; and generating at least one new medical image that is used for training a machine learning model for the medical images by transforming at least one medical image of the first medical image or the second medical image based on a result of the non-linear registration processing.

According to still another aspect of the present disclosure, there is provided a trained model that is trained by using a new medical image as a learning image, the new medical image being generated by transforming, based on a result of non-linear registration processing performed on a first medical image and a second medical image among a plurality of medical images, at least one medical image of the first medical image or the second medical image.

According to the technique of the present disclosure, it is possible to provide an image processing apparatus, an operation method of an image processing apparatus, an operation program of an image processing apparatus, and a trained model capable of generating a comprehensive learning image in which a form having an anatomical structure is maintained.

BRIEF DESCRIPTION OF THE DRAWINGS

Exemplary embodiments according to the technique of the present disclosure will be described in detail based on the following figures, wherein:

FIG. 1 is a diagram illustrating an image processing apparatus and the like;

FIG. 3 is a block diagram illustrating a processing unit of a CPU of the image processing apparatus;

FIGS. 8A and 8B are diagrams illustrating processing of the new image generation unit, FIG. 8A illustrates a case where a class of a first normalization image is "A", and FIG. 8B illustrates a case where a class of a first normalization image is "B";

FIGS. 9A and 9B are diagrams illustrating processing of the new image generation unit, FIG. 9A illustrates a case where a class of a second normalization image is "A", and FIG. 9B illustrates a case where a class of a second normalization image is "B";

FIG. 11 is a flowchart illustrating a processing procedure of the image processing apparatus;

FIG. 12 is a flowchart illustrating a processing procedure of the image processing apparatus;

FIG. 14 is a diagram illustrating another example of dementia opinion information;

FIG. 15 is a diagram illustrating still another example of dementia opinion information; and FIG. 16 is a diagram illustrating another example of processing of the new image generation unit.

DETAILED DESCRIPTION

Figure 1:
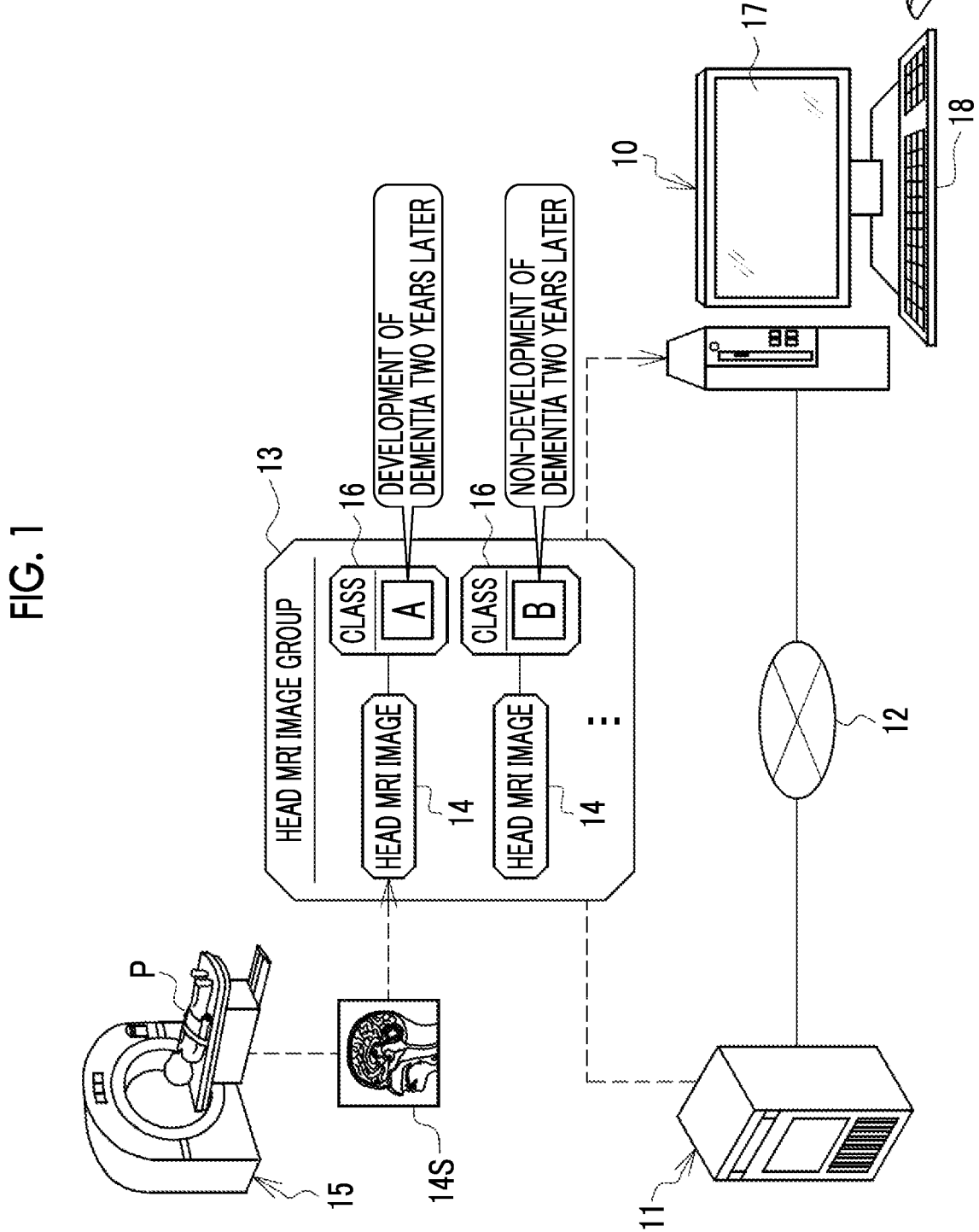

As illustrated in FIG. 1 as an example, an image processing apparatus 10 is connected to an image database server 11 via a network 12. The image database server 11 stores and manages various medical images uploaded from a plurality of medical facilities via the network 12. The network 12 is, for example, a wide area network (WAN) such as the Internet or a public communication network. In a case where the WAN is used, it is preferable to configure a virtual private network (VPN) or to use a communication protocol having a high security level such as a hypertext transfer protocol secure (HTTPS) in consideration of information security.

The image processing apparatus 10 receives a head magnetic resonance imaging (MRI) image group 13 that is distributed from the image database server 11. The head MRI image group 13 includes a plurality of head MRI images 14 that are allowed to be provided from medical facilities, for example, head MRI images 14 that are captured at a plurality of medical facilities from ten years ago to two years ago. The head MRI image 14 is obtained by imaging a head of a patient P by an MRI apparatus 15. The head MRI image 14 is voxel data representing a three-dimensional shape of the head of the patient P. In FIG. 1, a head MRI image 14S having a sagittal cross section is illustrated. The head MRI image 14 is an example of a "medical image" and an "image in which a head of a patient appears" according to the technique of the present disclosure.

A class 16 is associated with the head MRI image 14, and thus the head MRI images 14 are classified into classes. In the class 16, "A" is registered in a case where the patient P of the head MRI image 14 develops dementia two years later, and "B" is registered in a case where the patient P of the head MRI image 14 does not develop dementia two years later. The registration of the class 16 is performed by a doctor in charge of the patient P.

The image processing apparatus 10 is, for example, a desktop personal computer, and includes a display 17 and an input device 18. The input device 18 is a keyboard, a mouse, a touch panel, a microphone, or the like. An operator of the image processing apparatus 10 transmits a distribution request of the head MRI image group 13 to the image database server 11 by operating the input device 18. The image database server 11 searches for the head MRI image group 13 of which the distribution request is received, and distributes the head MRI image group 13 to the image processing apparatus 10.

Figure 2:
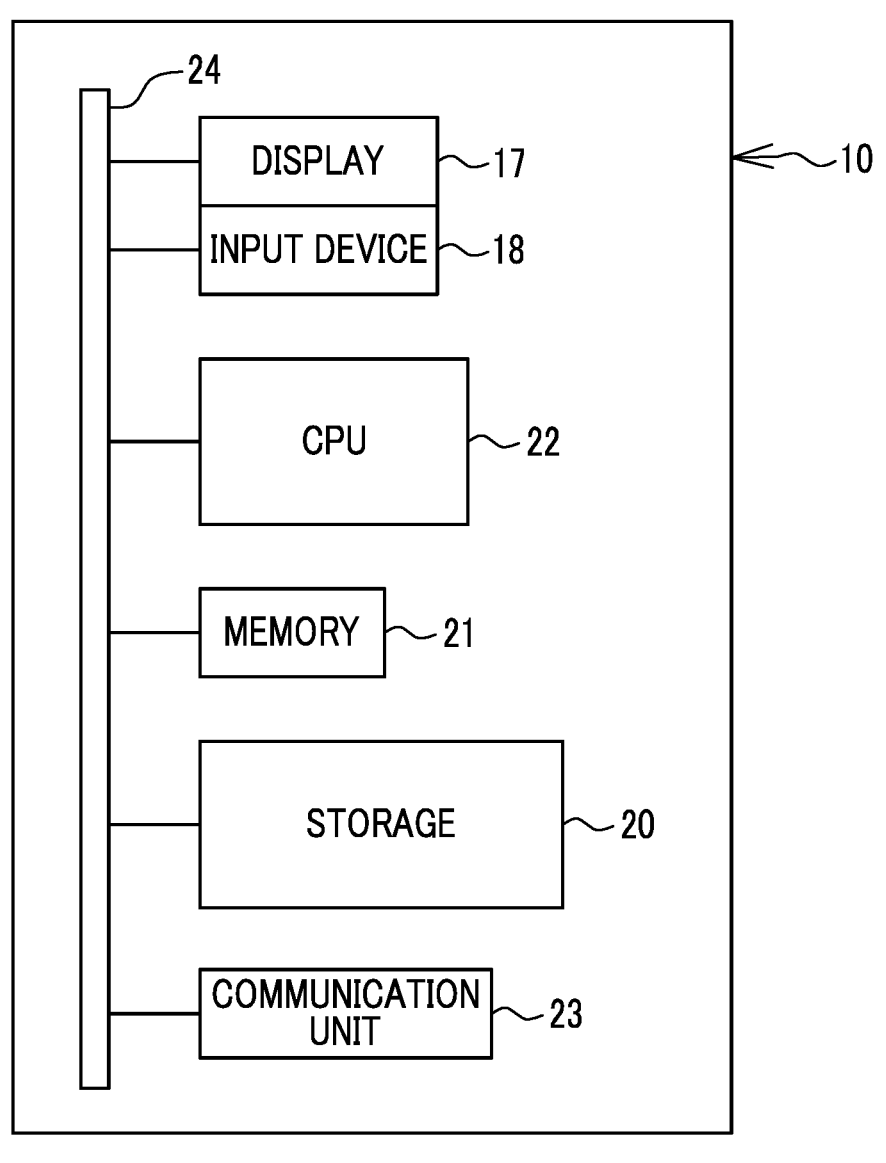
FIG. 2 is a block diagram illustrating a computer including the image processing apparatus.

As illustrated in FIG. 2 as an example, a computer including the image processing apparatus 10 includes a storage 20, a memory 21, a central processing unit (CPU) 22, and a communication unit 23, in addition to the display 17 and the input device 18. The components are connected to each other via a bus line 24. The CPU 22 is an example of a "processor" according to the technique of the present disclosure.

The storage 20 is a hard disk drive that is built in the computer including the image processing apparatus 10 or is connected via a cable or a network. Alternatively, the storage 20 is a disk array in which a plurality of hard disk drives are connected in series. The storage 20 stores a control program such as an operating system, various application programs, and various data associated with the programs. A solid state drive may be used instead of the hard disk drive.

The memory 21 is a work memory which is necessary to execute processing by the CPU 22. The CPU 22 loads the program stored in the storage 20 into the memory 21, and executes processing according to the program. Thereby, the CPU 22 collectively controls each unit of the computer. The communication unit 23 controls transmission of various types of information to an external apparatus such as the image database server 11. The memory 21 may be built in the CPU 22.

Figure 3:
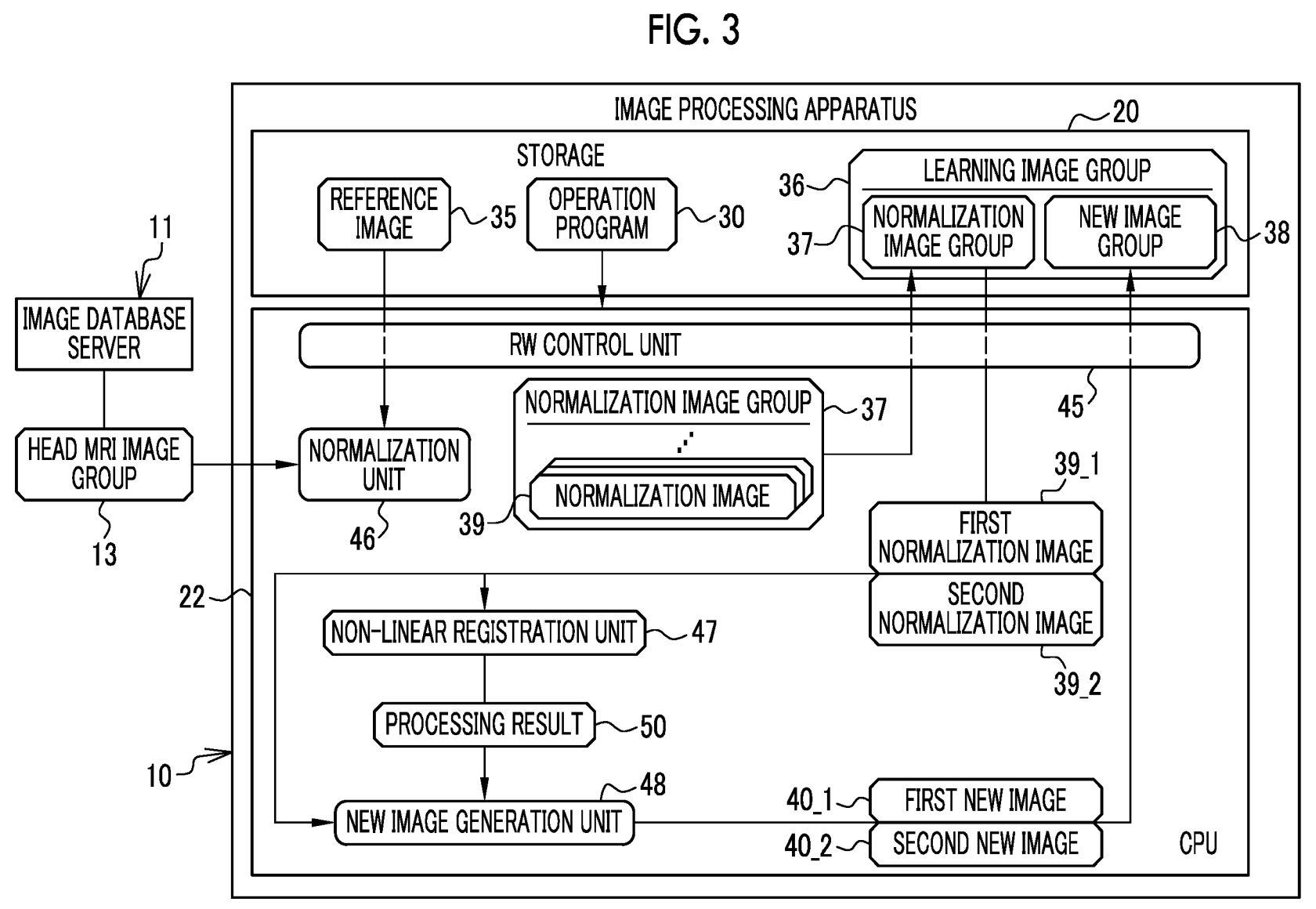

As illustrated in FIG. 3 as an example, an operation program 30 is stored in the storage 20 of the image processing apparatus 10. The operation program 30 is an application program for causing the computer to function as the image processing apparatus 10. That is, the operation program 30 is an example of "the operation program of the image processing apparatus" according to the technique of the present disclosure.

The storage 20 also stores a reference head MRI image (hereinafter, abbreviated as a reference image) 35 and a learning head MRI image group (hereinafter, abbreviated as a learning image group) 36. The learning image group 36 is a set of a plurality of learning head MRI images (hereinafter, abbreviated as learning images) 81 (refer to FIG. 10) used for training a dementia opinion derivation model 80 (refer to FIG. 10). The learning image group 36 includes a normalization head MRI image group (hereinafter, abbreviated as a normalization image group) 37 and a new head MRI image group (hereinafter, abbreviated as a new image group) 38. The normalization image group 37 includes a plurality of normalization head MRI images (hereinafter, abbreviated as normalization images) 39. The new image group 38 includes a plurality of first new head MRI images (hereinafter, abbreviated as first new images) 40_1 and a plurality of second new head MRI images (hereinafter, abbreviated as second new images) 40_2 (refer to FIG. 10).

In a case where the operation program 30 is started, the CPU 22 of the computer including the image processing apparatus 10 functions as a read/write (hereinafter, abbreviated as RW) control unit 45, a normalization unit 46, a non-linear registration unit 47, and a new image generation unit 48, in cooperation with the memory 21 and the like.

The RW control unit 45 controls storing of various types of data in the storage 20 and reading of various types of data in the storage 20. For example, the RW control unit 45 reads the reference image 35 from the storage 20, and outputs the read reference image 35 to the normalization unit 46. In addition, the RW control unit 45 receives the normalization image group 37 from the normalization unit 46, and stores the received normalization image group 37 in the storage 20, as a part of the learning image group 36. Further, the RW control unit 45 reads the first normalization image 39_1 and the second normalization image 39_2, which are two normalization images 39 among the plurality of normalization images 39 of the normalization image group 37, from the storage 20, and outputs the read first normalization image 39_1 and the read second normalization image 39_2 to the non-linear registration unit 47 and the new image generation unit 48. The first normalization image 39_1 and the second normalization image 39_2 are normalization images 39 of two patients P having the same attributes such as a gender and an age. The normalization image 39 is associated with the class 16 based on the original head MRI image 14 (refer to FIGS. 8A to 9B).

The normalization unit 46 performs normalization processing of matching the head MRI image 14 with the reference image 35, and sets the head MRI image 14 as the normalization image 39. The normalization unit 46 performs normalization processing on all of the plurality of head MRI images 14 included in the head MRI image group 13. Thereby, a plurality of normalization images 39 corresponding to the plurality of head MRI images 14 included in the head MRI image group 13 are generated. The normalization unit 46 outputs a normalization image group 37 including the plurality of normalization images 39 to the RW control unit 45.

The reference image 35 is a head MRI image in which a brain having a reference shape, a reference size, and a reference shade (pixel value) appears. The reference image 35 is, for example, an image generated by averaging head MRI images 14 of a plurality of healthy persons, or an image generated by computer graphics. The reference image 35 is an example of a "reference medical image" according to the technique of the present disclosure.

The non-linear registration unit 47 performs non-linear registration processing on the first normalization image 39_1 and the second normalization image 39_2. The non-linear registration unit 47 outputs a processing result 50, which is a result of the non-linear registration processing, to the new image generation unit 48.

The new image generation unit 48 generates a first new image 40_1 from the first normalization image 39_1 by transforming the first normalization image 39_1 based on the processing result 50, and generates a second new image 40_2 from the second normalization image 39_2 by transforming the second normalization image 39_2 based on the processing result 50. The new image generation unit 48 outputs the first new image 40_1 and the second new image 40_2 to the RW control unit 45. The RW control unit 45 stores the first new image 40_1 and the second new image 40_2 in the storage 20, as a part of the new image group 38 and a part of the learning image group 36. The first new image 40_1 is an example of a "first new medical image" according to the technique of the present disclosure. In addition, the second new image 40_2 is an example of a "second new medical image" according to the technique of the present disclosure.

Figure 4:
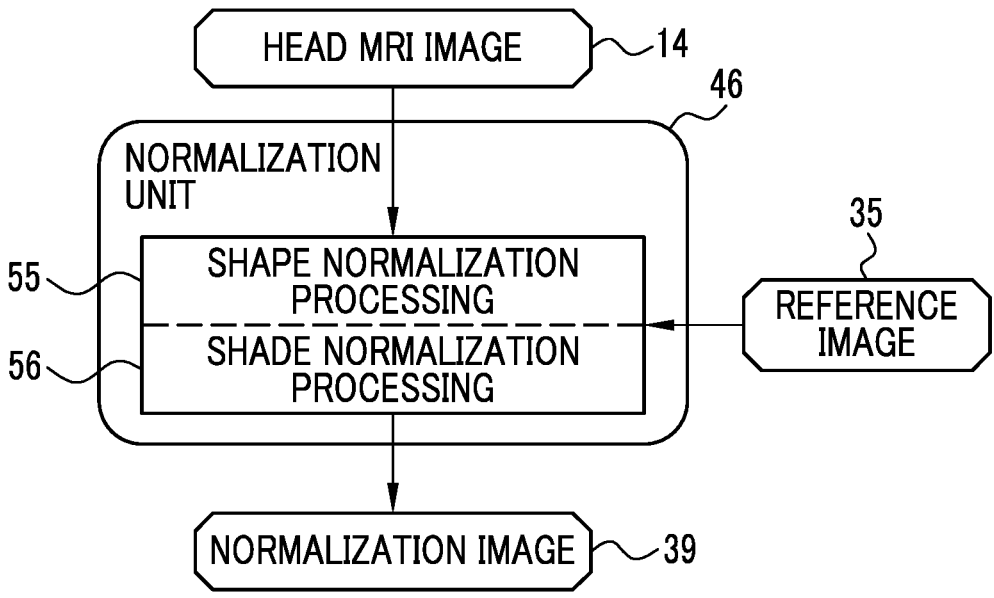
FIG. 4 is a diagram illustrating processing of a normalization unit.

As illustrated in FIG. 4 as an example, the normalization unit 46 performs, as normalization processing, shape normalization processing 55 and shade normalization processing 56 on the head MRI image 14. The shape normalization processing 55 is processing of extracting, for example, landmarks serving as references for registration from the head MRI image 14 and the reference image 35, and performing parallel displacement, rotation, and/or enlargement/reduction of the head MRI image 14 in accordance with the reference image 35 such that a correlation between the landmark of the head MRI image 14 and the landmark of the reference image 35 is maximized. The shade normalization processing 56 is, for example, processing of correcting a shade histogram of the head MRI image 14 in accordance with a shade histogram of the reference image 35.

Figure 5:
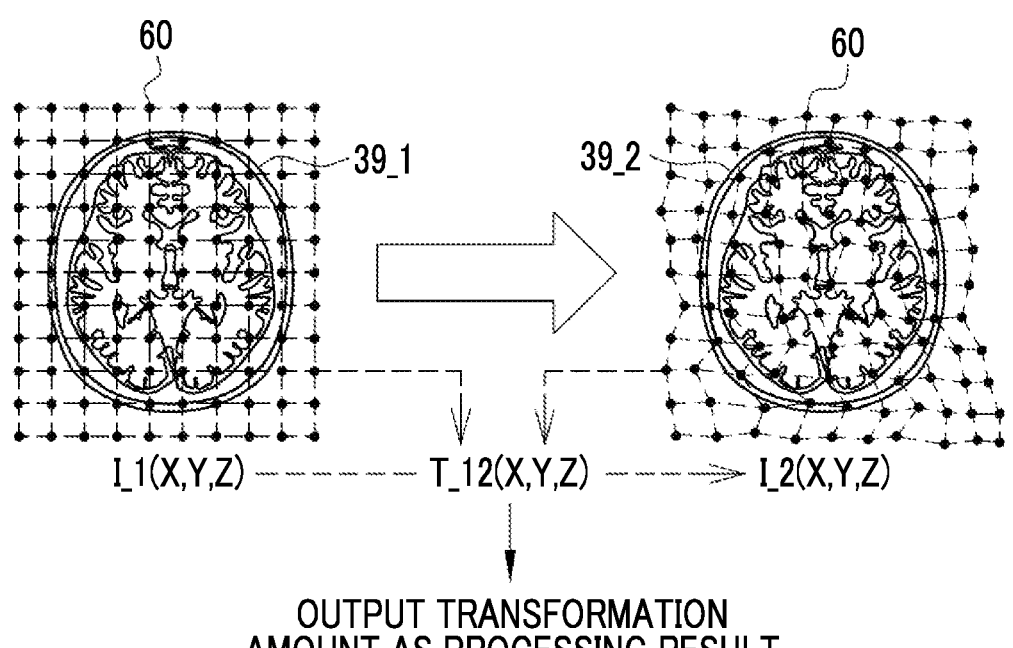
FIG. 5 is a diagram illustrating processing of a non-linear registration unit.

As illustrated in FIG. 5 as an example, in a case where the first normalization image 39_1 (denoted as I_1 (X, Y, Z)) is non-linearly registered with the second normalization image 39_2 (denoted as I_2 (X, Y, Z)), the non-linear registration unit 47 sets, on the first normalization image 39_1, a plurality of control points 60 which are arranged in a grid pattern at equal intervals. In addition, the non-linear registration unit 47 moves each control point 60 to a position at which a local similarity between the first normalization image 39_1 and the second normalization image 39_2 is increased. The non-linear registration unit 47 derives, from a movement amount of each control point 60, a transformation amount T_12 (X, Y, Z) of each pixel in a case where the first normalization image 39_1 is registered with the second normalization image 39_2, by using an interpolation approximation curve such as a B-Spline curve. The non-linear registration unit 47 outputs the derived transformation amount T_12 (X, Y, Z) as a processing result 50.

Figure 6:
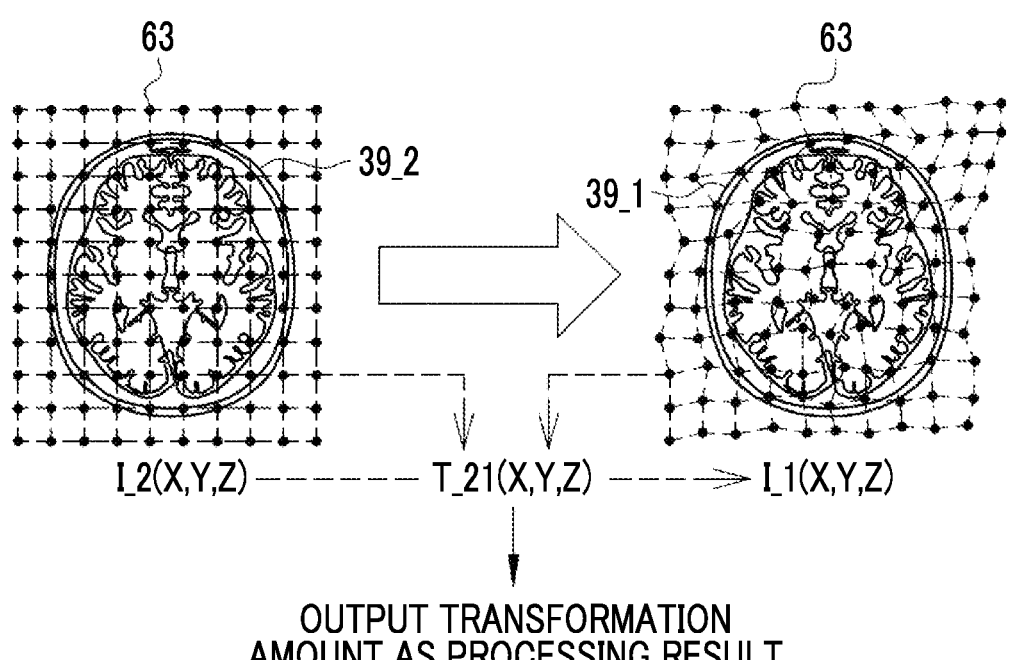
FIG. 6 is a diagram illustrating processing of the non-linear registration unit.

Further, as illustrated in FIG. 6 as an example, in a case where the second normalization image 39_2 is non-linearly registered with the first normalization image 39_1, the non-linear registration unit 47 sets, on the second normalization image 39_2, control points 63 which are same as the control points 60. In addition, the non-linear registration unit 47 moves each control point 63 as in the case of FIG. 5. As in the case of FIG. 5, the non-linear registration unit 47 derives, from a movement amount of each control point 63, a transformation amount T_21 (X, Y, Z) of each pixel in a case where the second normalization image 39_2 is registered with the first normalization image 39_1. The non-linear registration unit 47 outputs the derived transformation amount T_21 (X, Y, Z) as a processing result 50. In the following, (X, Y, Z) may be omitted.

FIG. 5 and FIG. 6 illustrate a state where the control points 60 and 63 are set in a two-dimensional shape on the first normalization image 39_1 and the second normalization image 39_2 having axial cross sections. On the other hand, the control points 60 and 63 are actually set in a three-dimensional shape. The transformation amount T_12 (X, Y, Z) and the transformation amount T_21 (X, Y, Z) have an inverse function relationship with each other. Thus, in a case where one of the transformation amount T_12 (X, Y, Z) and the transformation amount T_21 (X, Y, Z) is derived by a method using the control points 60 or 63, the other of the transformation amount T_12 (X, Y, Z) and the transformation amount T_21 (X, Y, Z) may be derived by obtaining an inverse function of one of the transformation amount T_12 (X, Y, Z) and the transformation amount T_21 (X, Y, Z).

Figure 7:
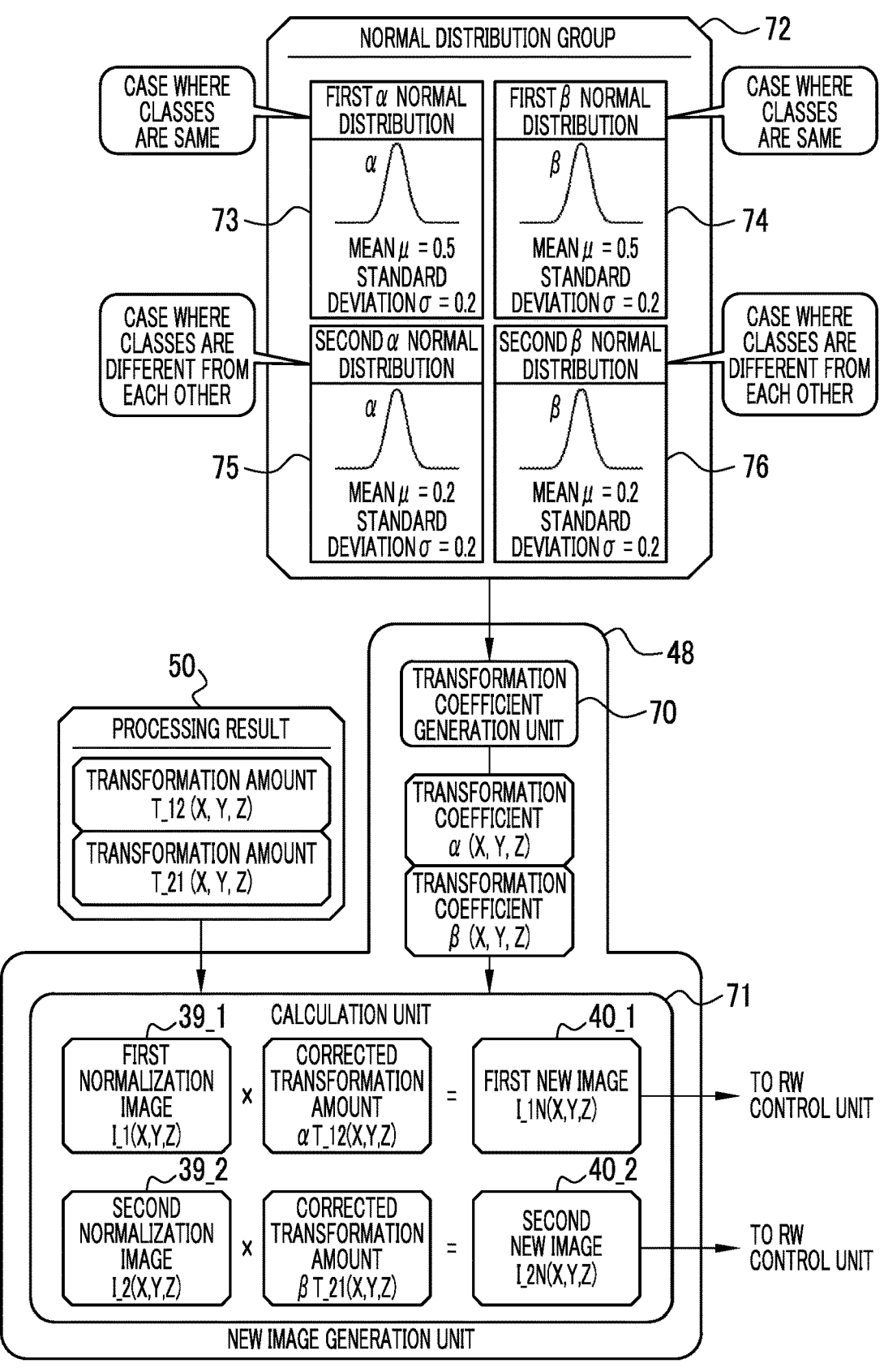
FIG. 7 is a diagram illustrating details of a new image generation unit.

As illustrated in FIG. 7 as an example, the new image generation unit 48 includes a transformation coefficient generation unit 70 and a calculation unit 71. The transformation coefficient generation unit 70 generates transformation coefficients α (X, Y, Z) and β (X, Y, Z) based on a normal distribution group 72. The transformation coefficient generation unit 70 outputs the generated transformation coefficients α (X, Y, Z) and β (X, Y, Z) to the calculation unit 71. The transformation coefficients α (X, Y, Z) and β (X, Y, Z) are values larger than 0 and smaller than 1 (0<α, β<1).

The normal distribution group 72 includes a first α normal distribution 73, a first β normal distribution 74, a second α normal distribution 75, and a second β normal distribution 76. The transformation coefficient generation unit 70 outputs, as the transformation coefficients α (X, Y, Z) and β (X, Y, Z), a random number according to any one normal distribution of the first α normal distribution 73, the first β normal distribution 74, the second α normal distribution 75, and the second β normal distribution 76. The frequency of occurrence of the random number is, for example, for each pixel.

The first α normal distribution 73 and the first β normal distribution 74 are used in a case where the classes 16 of the first normalization image 39_1 and the second normalization image 39_2 are the same. On the other hand, the second α normal distribution 75 and the second β normal distribution 76 are used in a case where the classes 16 of the first normalization image 39_1 and the second normalization image 39_2 are different from each other. The first α normal distribution 73 and the first β normal distribution 74 have a mean μ=0.5 and a standard deviation σ=0.2. On the other hand, the second α normal distribution 75 and the second β normal distribution 76 have a mean μ=0.2 and a standard deviation σ=0.2. That is, the means μ of the second α normal distribution 75 and the second β normal distribution 76 are smaller than the means μ of the first α normal distribution 73 and the first β normal distribution 74. Therefore, values of the transformation coefficients α (X, Y, Z) and β (X, Y, Z) are changed depending on whether the classes 16 of the first normalization image 39_1 and the second normalization image 39_2 are the same or different from each other. The first α normal distribution 73 and the first β normal distribution 74 are examples of "normal distributions in a case where the classes of the first medical image and the second medical image are the same" according to the technique of the present disclosure. In addition, the second α normal distribution 75 and the second β normal distribution 76 are examples of "normal distributions in a case where the classes of the first medical image and the second medical image are different from each other" according to the technique of the present disclosure.

The calculation unit 71 multiplies the transformation coefficient α (X, Y, Z) by the transformation amount T_12 (X, Y, Z) from the first normalization image 39_1 to the second normalization image 39_2, and sets a value obtained by the multiplication, as a corrected transformation amount αT_12 (X, Y, Z). In addition, the calculation unit 71 multiplies the transformation coefficient β (X, Y, Z) by the transformation amount T_21 (X, Y, Z) from the second normalization image 39_2 to the first normalization image 39_1, and sets a value obtained by the multiplication, as a corrected transformation amount βT_21 (X, Y, Z). The calculation unit 71 sets the first normalization image 39_1 as the first new image 40_1 (denoted as I_1N (X, Y, Z)) by applying the corrected transformation amount αT_12 (X, Y, Z) to the first normalization image 39_1. In addition, the calculation unit 71 sets the second normalization image 39_2 as the second new image 40_2 (denoted as I_2N (X, Y, Z)) by applying the corrected transformation amount (βT_21 (X, Y, Z) to the second normalization image 39_2.

As illustrated in FIGS. 8A and 8B as an example, the new image generation unit 48 sets the class of the first new image 40_1 to be the same as the class 16 of the first normalization image 39_1. More specifically, in a case where the class 16 of the first normalization image 39_1 is "A" as illustrated in FIG. 8A, the class 16 of the first new image 40_1 is also set to "A". Further, in a case where the class 16 of the first normalization image 39_1 is "B" as illustrated in FIG. 8B, the class 16 of the first new image 40_1 is also set to "B".

Similarly, as illustrated in FIGS. 9A and 9B as an example, the new image generation unit 48 sets the class of the second new image 40_2 to be the same as the class 16 of the second normalization image 39_2. More specifically, in a case where the class 16 of the second normalization image 39_2 is "A" as illustrated in FIG. 9A, the class 16 of the second new image 40_2 is also set to "A". In addition, in a case where the class 16 of the second normalization image 39_2 is "B" as illustrated in FIG. 9B, the class 16 of the second new image 40_2 is also set to "B".

Figure 10:
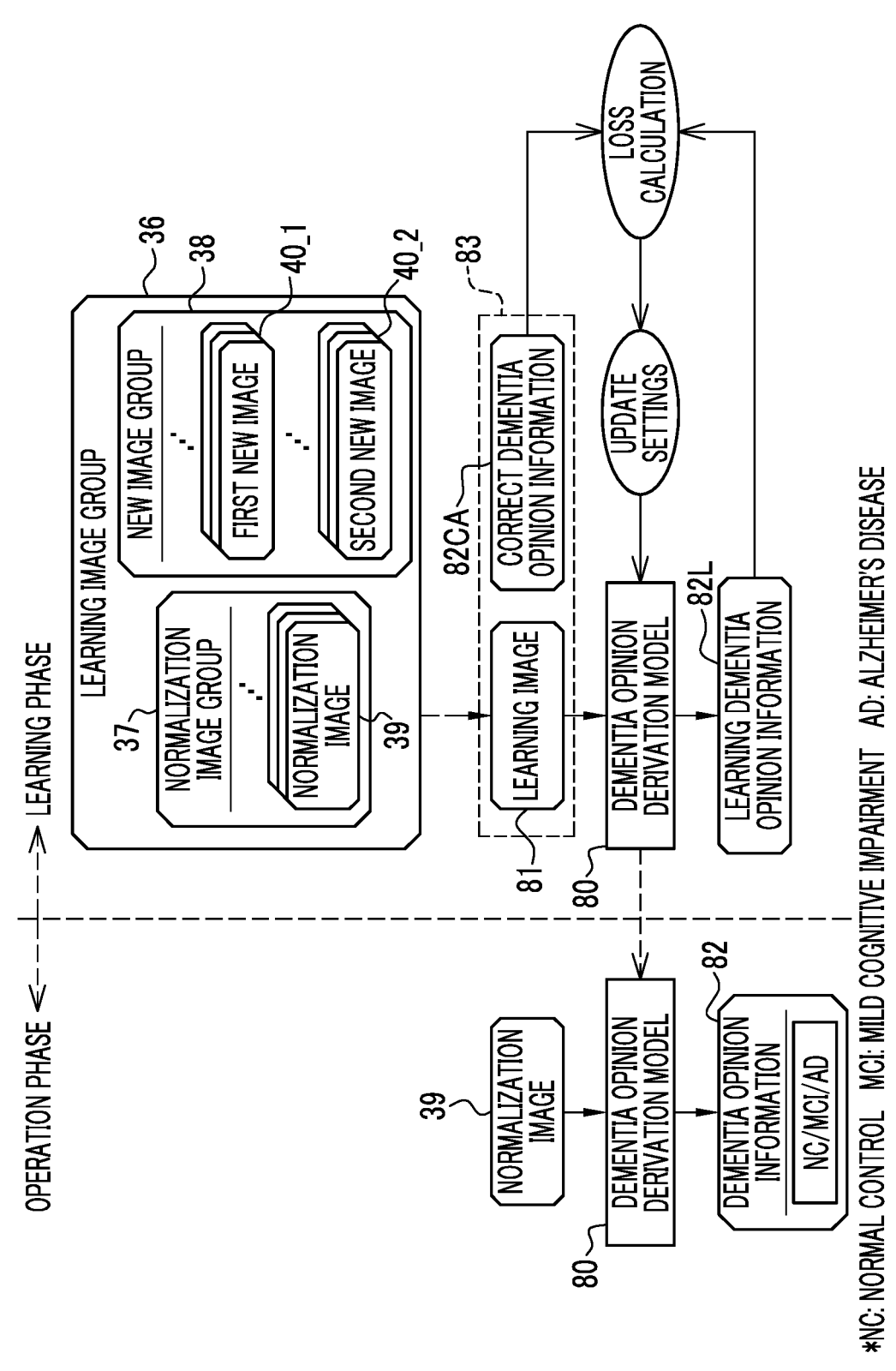
FIG. 10 is a diagram illustrating an outline of processing in a learning phase and an operation phase of a dementia opinion derivation model.

As illustrated in FIG. 10 as an example, in the learning image group 36, the plurality of normalization images 39 included in the normalization image group 37, and one image among the plurality of first new images 40_1 and the plurality of second new images 40_2 included in the new image group 38 are provided as the learning images 81 of the dementia opinion derivation model 80. The dementia opinion derivation model 80 is a machine learning model that receives the normalization images 39 as input data and outputs dementia opinion information 82 as output data, the dementia opinion information 82 being information representing a dementia opinion of the patient P of the normalization images 39. The dementia opinion information 82 is any one of normal control (NC), mild cognitive impairment (MCI), and Alzheimer's disease (AD).

The dementia opinion derivation model 80 is configured by, for example, any method of a neural network, a support vector machine, and boosting. In a learning phase, the dementia opinion derivation model 80 is trained by inputting, to the dementia opinion derivation model 80, learning data 83 which is a set of the learning image 81 and correct dementia opinion information 82CA. The correct dementia opinion information 82CA is a dementia opinion obtained by actually diagnosing the patient P of the learning images 81 by the doctor in charge of the patient P.

In the learning phase, the learning images 81 are input to the dementia opinion derivation model 80. The dementia opinion derivation model 80 outputs learning dementia opinion information 82L in response to the learning images 81. A loss calculation of the dementia opinion derivation model 80 is performed based on the learning dementia opinion information 82L and the correct dementia opinion information 82CA. In addition, update settings of various coefficients of the dementia opinion derivation model 80 are performed according to a result of the loss calculation, and the dementia opinion derivation model 80 is updated according to the update settings.

In the learning phase, while exchanging the learning data 83, a series of pieces of processing, which includes inputting of the learning image 81 to the dementia opinion derivation model 80, outputting of the learning dementia opinion information 82L from the dementia opinion derivation model 80, the loss calculation, the update settings, and updating of the dementia opinion derivation model 80, is repeatedly performed. The repetition of the series of pieces of processing is ended in a case where prediction accuracy of the learning dementia opinion information 82L with respect to the correct dementia opinion information 82CA reaches a predetermined set level. The dementia opinion derivation model 80 of which the prediction accuracy reaches the set level in this way is used as a trained model in an operation phase.

Next, an operation according to the configuration will be described with reference to flowcharts illustrated in FIG. 11 and FIG. 12. First, in a case where the operation program 30 is started in the image processing apparatus 10, as illustrated in FIG. 3, the CPU 22 of the image processing apparatus 10 functions as the RW control unit 45, the normalization unit 46, the non-linear registration unit 47, and the new image generation unit 48. As illustrated in FIG. 7, the new image generation unit 48 includes the transformation coefficient generation unit 70 and the calculation unit 71.

As illustrated in FIG. 11 as an example, first, the normalization unit 46 receives the head MRI image group 13 from the image database server 11 (step ST100). In addition, as illustrated in FIG. 4, the normalization unit 46 performs normalization processing (shape normalization processing 55 and shade normalization processing 56) of matching the head MRI image 14 with the reference image 35 (step ST110). Thereby, the head MRI image 14 is set as the normalization image 39. The normalization image 39 is output from the normalization unit 46 to the RW control unit 45, and is stored in the storage 20 by the RW control unit 45 (step ST120).

As illustrated in FIG. 12 as an example, the RW control unit 45 reads the first normalization image 39_1 and the second normalization image 39_2 from the storage 20 (step ST200). The first normalization image 39_1 and the second normalization image 39_2 are output from the RW control unit 45 to the non-linear registration unit 47 and the new image generation unit 48.

As illustrated in FIG. 5, the non-linear registration unit 47 performs non-linear registration processing of non-linearly registering the first normalization image 39_1 with the second normalization image 39_2. In addition, as illustrated in FIG. 6, the non-linear registration unit 47 performs non-linear registration processing of non-linearly registering the second normalization image 39_2 with the first normalization image 39_1 (step ST210). The transformation amounts T_12 and T_21 derived by the non-linear registration processing are output from the non-linear registration unit 47 to the new image generation unit 48, as the processing result 50.

As illustrated in FIG. 7, the new image generation unit 48 applies, to the first normalization image 39_1, the corrected transformation amount $\alpha$T_12 obtained by multiplying the transformation amount T_12 by the transformation coefficient $\alpha$, and generates the first new image 40_1 from the first normalization image 39_1. Further, the new image generation unit 48 applies, to the second normalization image 39_2, the corrected transformation amount ($\beta$T_21 obtained by multiplying the transformation amount T_21 by the transformation coefficient $\beta$, and generates the second new image 40_2 from the second normalization image 39_2 (step ST220). The first new image 40_1 and the second new image 40_2 are output from the new image generation unit 48 to the RW control unit 45, and are stored in the storage 20 by the RW control unit 45 (step ST230). A series of pieces of processing of step ST200 to step ST230 is repeatedly performed while a combination of the first normalization image 39_1 and the second normalization image 39_2 is changed, as long as the total number of the images in the learning image group 36, that is, the number of the learning images 81 does not reach a target number (NO in step ST240).

As described above, the CPU 22 of the image processing apparatus 10 includes the non-linear registration unit 47 and the new image generation unit 48. The non-linear registration unit 47 performs non-linear registration processing on the first normalization image 39_1 and the second normalization image 39_2 among the plurality of normalization images 39. The new image generation unit 48 generates the first new image 40_1 and the second new image 40_2 used for training the dementia opinion derivation model 80 by transforming the first normalization image 39_1 and the second normalization image 39_2 based on the processing result 50 of the non-linear registration processing.

The first new image 40_1 and the second new image 40_2 are generated based on the first normalization image 39_1 and the second normalization image 39_2. Therefore, it is possible to increase a variation of the learning image 81, as compared to a method described in <C. Shorten, T. M. Khoshgofttar: A survey on Image Data Augmentation, Journal of Big Data, 2019>, which generates the learning image 81 from one image. In addition, the first new image 40_1 and the second new image 40_2 are not obtained by mixing pixel values of the first normalization image 39_1 and the second normalization image 39_2. Thus, a form having an anatomical structure is not blurred as in a method described in <Y. Tokozume, Y. Ushiku, T. Harada: Between-class Learning for Image Classification, CVPR, 2018>. Therefore, according to the technique of the present disclosure, it is possible to generate a comprehensive learning image 81 in which a form having an anatomical structure is maintained.

The new image generation unit 48 sets the first normalization image 39_1 as the first new image 40_1 by applying, to the first normalization image 39_1, the corrected transformation amount $\alpha T\_12$ obtained by multiplying the transformation amount $T\_12$ from the first normalization image 39_1 to the second normalization image 39_2 in the non-linear registration processing by the transformation coefficient $\alpha$. Further, the new image generation unit 48 sets the second normalization image 39_2 as the second new image 40_2 by applying, to the second normalization image 39_2, the corrected transformation amount $\beta T\_21$ obtained by multiplying the transformation amount $T\_21$ from the second normalization image 39_2 to the first normalization image 39_1 in the non-linear registration processing by the transformation coefficient $\beta$. Therefore, in a case where the transformation coefficients $\alpha$ and $\beta$ are set to appropriate values, the desired first new image 40_1 and the desired second new image 40_2 can be obtained. For example, in a case where the transformation coefficient $\alpha$ is set to a value close to 0, the first new image 40_1 that is relatively similar to the first normalization image 39_1 is obtained. On the contrary, in a case where the transformation coefficient $\alpha$ is set to a value close to 1, the first new image 40_1 that is relatively similar to the second normalization image 39_2 is obtained.

The head MRI image 14 and the normalization image 39 are classified into classes. The new image generation unit 48 changes the values of the transformation coefficients $\alpha$ and $\beta$ depending on whether the classes 16 of the first normalization image 39_1 and the second normalization image 39_2 are the same or different from each other. Therefore, it is possible to generate the first new image 40_1 and the second new image 40_2 that are suitable depending on whether the classes 16 of the first normalization image 39_1 and the second normalization image 39_2 are the same or different from each other.

Figure 13:
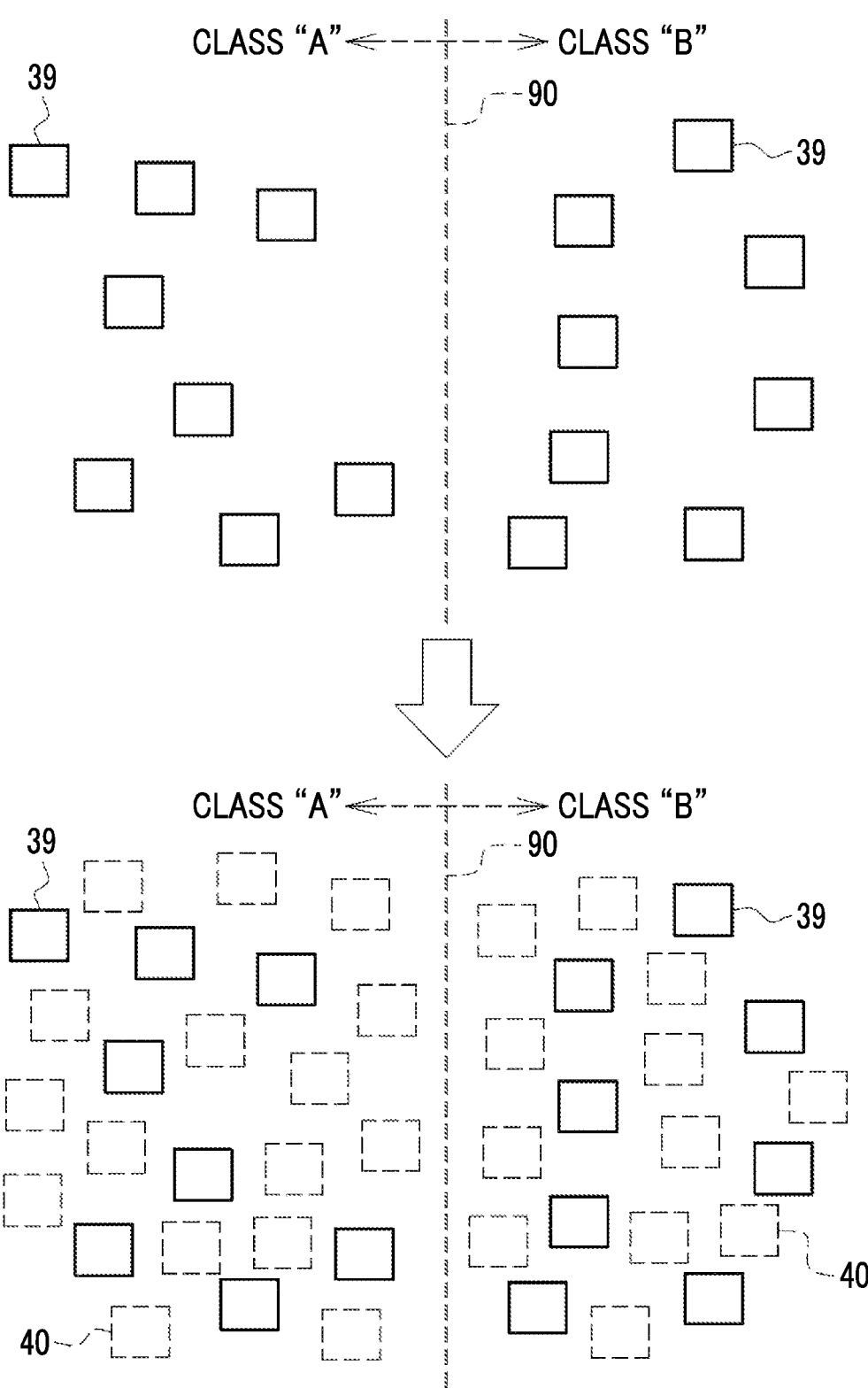
FIG. 13 is a diagram schematically illustrating a data distribution of images in each class.

As illustrated in FIGS. 8A to 9B, the new image generation unit 48 sets the class of the first new image 40_1 to be the same as the class 16 of the first normalization image 39_1, and sets the class of the second new image 40_2 to be the same as the class 16 of the second normalization image 39_2. Therefore, the class 16 that is suitable for a purpose of each of the first new image 40_1 and the second new image 40_2 can be associated. In addition, as schematically illustrated in FIG. 13, the new image 40 can be used to fill a data blank in each class 16 of "A" and "B" that cannot be filled by only the normalization image 39. Further, the new image 40 can be used to fill a data blank near a boundary 90 of each class 16 of "A" and As illustrated in FIG. 7, the transformation coefficients $\alpha$ and $\beta$ are random numbers according to any one of the normal distributions 73 to 76. Therefore, it is possible to generate the first new image 40_1 and the second new image 40_2 that cannot be predicted from the first normalization image 39_1 and the second normalization image 39_2. Thereby, it is possible to increase a variation of the learning image 81.

As illustrated in FIG. 7, the means $\mu$ of the second $\alpha$ normal distribution 75 and the second $\beta$ normal distribution 76 in a case where the classes of the first normalization image 39_1 and the second normalization image 39_2 are different from each other are smaller than the means $\mu$ of the first $\alpha$ normal distribution 73 and the first $\beta$ normal distribution 74 in a case where the classes of the first normalization image 39_1 and the second normalization image 39_2 are the same. Therefore, in a case where the classes of the first normalization image 39_1 and the second normalization image 39_2 are different from each other, as compared with a case where the classes of the first normalization image 39_1 and the second normalization image 39_2 are the same, it is possible to generate the first new image 40_1, which is relatively similar to the first normalization image 39_1, and the second new image 40_2, which is relatively similar to the second normalization image 39_2. Therefore, even in a case where the class of the first new image 40_1 is set to be the same as the class 16 of the first normalization image 39_1 and the class of the second new image 40_2 is set to be the same as the class 16 of the second normalization image 39_2, there is no sense of incongruity.

As illustrated in FIG. 4, the normalization unit 46 performs normalization processing of matching the head MRI image 14 with the reference image 35, prior to non-linear registration processing. Therefore, after an individual difference of the patient P and an apparatus difference of the MRI apparatus 15 are substantially eliminated, subsequent processing can be performed. Thereby, it is possible to improve reliability of the dementia opinion information 82.

The dementia has become a social problem with the advent of an aging society in recent years. Therefore, it can be said that the present embodiment in which a medical image is the head MRI image 14 and a machine learning model for the medical image is the dementia opinion derivation model 80 which outputs the dementia opinion information 82 is a form matching with the current social problem. In addition, a form having an anatomical structure, such as a degree of atrophy of a hippocampus, a parahippocampal gyms, an amygdala, or the like, provides a particularly important key in the dementia opinion. Thus, an effect of capable of generating the learning image 81 in which a form having an anatomical structure is maintained can be further exhibited.

The dementia opinion information 82 is not limited to the content illustrated in FIG. 10 (normal control/mild cognitive impairment/Alzheimer's disease). For example, as in the dementia opinion information 95 illustrated in FIG. 14, the dementia opinion information may indicate whether a degree of progression of dementia of the patient P one year later is fast or slow. Alternatively, as in the dementia opinion information 98 illustrated in FIG. 15, the dementia opinion information may be a type of dementia, such as Alzheimer's disease, dementia with Lewy body, or vascular dementia.

The embodiment in which both the first new image 40_1 and the second new image 40_2 are generated has been illustrated. On the other hand, the present disclosure is not limited thereto. As illustrated in FIG. 16 as an example, only one of the first new image 40_1 and the second new image 40_2 may be generated, such as generating of only the first new image 40_1. In the case of FIG. 16, the normal distribution group 72 includes only the first $\alpha$ normal distribution 73 and the second α normal distribution 75. In addition, the processing result 50 includes only the transformation amount T_12 (X, Y, Z). The transformation coefficient generation unit 70 generates only the transformation coefficient α (X, Y, Z). The calculation unit 71 generates only the first new image 40_1 from the first normalization image 39_1.

The non-linear registration processing may be performed on two new images 40, and the first new image 40_1 and the second new image 40_2 may be generated based on the processing result 50. Similarly, the first new image 40_1 and the second new image 40_2 may be generated from the normalization image 39 and the new image 40.

The class 16 is not limited to whether or not the patient develops dementia two years after in the example. For example, as in the dementia opinion information 82, any one of normal control/mild cognitive impairment/Alzheimer's disease may be registered as the class 16.

The transformation coefficients α and β may be fixed values instead of random numbers according to the normal distribution. In addition, the means μ of the first α normal distribution 73 and the first β normal distribution 74 in a case where the classes of the first normalization image 39_1 and the second normalization image 39_2 are the same are not limited to 0.5 in the example. For example, the mean μ may be 0.4 or 0.6. Similarly, the means μ of the second α normal distribution 75 and the second β normal distribution 76 in a case where the classes of the first normalization image 39_1 and the second normalization image 39_2 are different from each other are not limited to 0.2 in the example. For example, the mean μ may be 0.1 or 0.3. The standard deviation a is also not limited to 0.2 in the example.

The training of the dementia opinion derivation model 80 illustrated in FIG. 10 may be performed by the image processing apparatus 10, or may be performed by an apparatus other than the image processing apparatus 10. Similarly, an operation of actually inputting the normalization image 39 to the dementia opinion derivation model 80 and outputting the dementia opinion information 82 from the dementia opinion derivation model 80 may also be performed in the image processing apparatus 10, or may be performed by an apparatus other than the image processing apparatus 10. In addition, the training of the dementia opinion derivation model 80 may be continued even after the operation.

The image database server 11 may perform some or all functions of each of the processing units 45 to 48. For example, the normalization unit 46 may be included in the CPU of the image database server 11, and the non-linear registration unit 47 and the new image generation unit 48 may be included in the CPU of the image processing apparatus 10.

The medical image is not limited to the head MRI image 14 in the example. The medical image may be a positron emission tomography (PET) image, a single photon emission computed tomography (SPECT) image, a computed tomography (CT) image, an endoscopic image, an ultrasound image, or the like.

The subject is not limited to the head in the example, and may be a chest, an abdomen, or the like. In addition, the disease is not limited to dementia in the example, and may be a heart disease, pneumonia, dyshepatia, or the like.

In the embodiment, for example, as a hardware structure of the processing unit that executes various processing, such as the RW control unit 45, the normalization unit 46, the non-linear registration unit 47, the new image generation unit 48, the transformation coefficient generation unit 70, and the calculation unit 71, the following various processors may be used. The various processors include, as described above, the CPU 22 which is a general-purpose processor that functions as various processing units by executing software (an operation program 30), a programmable logic device (PLD) such as a field programmable gate array (FPGA) which is a processor capable of changing a circuit configuration after manufacture, a dedicated electric circuit such as an application specific integrated circuit (ASIC) which is a processor having a circuit configuration specifically designed to execute specific processing, and the like.

One processing unit may be configured by one of these various processors, or may be configured by a combination of two or more processors having the same type or different types (for example, a combination of a plurality of FPGAs and/or a combination of a CPU and an FPGA). Further, the plurality of processing units may be configured by one processor.

As an example in which the plurality of processing units are configured by one processor, firstly, as represented by a computer such as a client and a server, a form in which one processor is configured by a combination of one or more CPUs and software and the processor functions as the plurality of processing units may be adopted. Secondly, as represented by system on chip (SoC), there is a form in which a processor that realizes the functions of the entire system including a plurality of processing units with one integrated circuit (IC) chip is used. As described above, the various processing units are configured by using one or more various processors as a hardware structure.

Further, as the hardware structure of the various processors, more specifically, an electric circuit (circuitry) in which circuit elements such as semiconductor elements are combined may be used.

The technique of the present disclosure can also appropriately combine the various embodiments and/or the various modification examples. In addition, the technique of the present disclosure is not limited to the embodiments, and various configurations may be adopted without departing from the scope of the present disclosure. Further, the technique of the present disclosure extends to a program and a storage medium for non-temporarily storing the program.

The described contents and the illustrated contents are detailed explanations of a part according to the technique of the present disclosure, and are merely examples of the technique of the present disclosure. For example, the descriptions related to the configuration, the function, the operation, and the effect are descriptions related to examples of a configuration, a function, an operation, and an effect of a part according to the technique of the present disclosure. Therefore, it goes without saying that, in the described contents and illustrated contents, unnecessary parts may be deleted, new components may be added, or replacements may be made without departing from the spirit of the technique of the present disclosure. Further, in order to avoid complications and facilitate understanding of the part according to the technique of the present disclosure, in the described contents and illustrated contents, descriptions of technical knowledge and the like that do not require particular explanations to enable implementation of the technique of the present disclosure are omitted.

In this specification, "A and/or B" is synonymous with "at least one of A or B". That is, "A and/or B" means that only A may be included, that only B may be included, or that a combination of A and B may be included. Further, in this specification, even in a case where three or more matters are expressed by being connected using "and/or", the same concept as "A and/or B" is applied.

All documents, patent applications, and technical standards mentioned in this specification are incorporated herein by reference to the same extent as in a case where each document, each patent application, and each technical standard are specifically and individually described by being incorporated by reference.

What is claimed is:

1. An image processing apparatus comprising:
a processor; and
a memory connected to or built in the processor,
wherein the processor is configured to
perform non-linear registration processing on a first medical image and a second medical image among a plurality of medical images to derive transformation amounts as a result of the non-linear registration processing, wherein the medical images are classified into classes,
generate transformation coefficients based on the classes of the first medical image and the second medical image,
multiply the transformation coefficients by the derived transformation amounts to obtain corrected transformation amounts, and
generate at least one new medical image that is used for training a machine learning model for the medical images by transforming at least one medical image of the first medical image or the second medical image using at least one of the corrected transformation amounts.

2. The image processing apparatus according to claim 1, wherein the transformation coefficients comprise a transformation coefficient $\alpha$ and a transformation coefficient $\beta$,
the transformation amounts comprise a transformation amount T_12 from the first medical image to the second medical image in the non-linear registration processing, and a transformation amount T_21 from the second medical image to the first medical image in the non-linear registration processing, and
the corrected transformation amounts comprise a corrected transformation amount $\alpha$T_12 obtained by multiplying the transformation amount T_12 by the transformation coefficient $\alpha$, and a corrected transformation amount $\beta$T_21 obtained by multiplying the transformation amount T_21 by the transformation coefficient $\beta$,
wherein the processor is configured to
set the first medical image as a first new medical image by applying, to the first medical image, the corrected transformation amount $\alpha$T_12, and
set the second medical image as a second new medical image by applying, to the second medical image, the corrected transformation amount $\beta$T_21.

3. The image processing apparatus according to claim 2, wherein
the processor is configured to change values of the transformation coefficients $\alpha$ and $\beta$ depending on whether the classes of the first medical image and the second medical image are the same or different from each other.

4. The image processing apparatus according to claim 3, wherein the processor is configured to
set a class of the first new medical image to be the same as the class of the first medical image, and set a class of the second new medical image to be the same as the class of the second medical image.

5. The image processing apparatus according to claim 2, wherein the transformation coefficients $\alpha$ and $\beta$ are random numbers according to a normal distribution.

6. The image processing apparatus according to claim 5, wherein
the processor is configured to
change values of the transformation coefficients $\alpha$ and $\beta$ depending on whether the classes of the first medical image and the second medical image are the same or different from each other, and
a mean of a normal distribution in a case where the classes of the first medical image and the second medical image are different from each other is smaller than a mean of a normal distribution in a case where the classes of the first medical image and the second medical image are the same.

7. The image processing apparatus according to claim 5, wherein
the processor is configured to
change values of the transformation coefficients $\alpha$ and $\beta$ depending on whether the classes of the first medical image and the second medical image are the same or different from each other,
set a class of the first new medical image to be the same as the class of the first medical image,
set a class of the second new medical image to be the same as the class of the second medical image, and
a mean of a normal distribution in a case where the classes of the first medical image and the second medical image are different from each other is smaller than a mean of a normal distribution in a case where the classes of the first medical image and the second medical image are the same.

8. The image processing apparatus according to claim 1, wherein the processor is configured to perform normalization processing of matching the first medical image and the second medical image with a reference medical image prior to the non-linear registration processing.

9. The image processing apparatus according to claim 1, wherein the medical image is an image in which a head of a patient appears, and
the machine learning model is a model that outputs a dementia opinion on the patient.

10. An operation method of an image processing apparatus, the method comprising:
performing non-linear registration processing on a first medical image and a second medical image among a plurality of medical images to derive transformation amounts as a result of the non-linear registration processing, wherein the medical images are classified into classes,
generating transformation coefficients based on the classes of the first medical image and the second medical image,
multiplying the transformation coefficients by the derived transformation amounts to obtain corrected transformation amounts; and
generating at least one new medical image that is used for training a machine learning model for the medical images by transforming at least one medical image of the first medical image or the second medical image using at least one of the corrected transformation amounts.

11. A non-transitory computer-readable storage medium storing an operation program of an image processing apparatus, the program causing a computer to execute a process comprising:

performing non-linear registration processing on a first medical image and a second medical image among a plurality of medical images to derive transformation amounts as a result of the non-linear registration processing, wherein the medical images are classified into classes, generating transformation coefficients based on the classes of the first medical image and the second medical image, multiplying the transformation coefficients by the derived transformation amounts to obtain corrected transformation amounts; and generating at least one new medical image that is used for training a machine learning model for the medical images by transforming at least one medical image of the first medical image or the second medical image using at least one of the corrected transformation amounts.

12. A non-transitory computer-readable storage medium storing a trained model that is trained by using a new medical image as a learning image, the new medical image being generated by transforming at least one medical image of a first medical image or a second medical image among a plurality of medical images using at least one of corrected transformation amounts, wherein the corrected transformation amounts is obtained by:

performing non-linear registration processing on the first medical image and the second medical image to derive transformation amounts as a result of the non-linear registration processing, wherein the medical images are classified into classes, generating transformation coefficients based on the classes of the first medical image and the second medical image, and multiplying the transformation coefficients by the derived transformation amounts to obtain the corrected transformation amounts.

* * * * *